United States Patent [19]

Steinhaus et al.

[11] Patent Number: 5,217,021
[45] Date of Patent: Jun. 8, 1993

[54] DETECTION OF CARDIAC ARRHYTHMIAS USING CORRELATION OF A CARDIAC ELECTRICAL SIGNALS AND TEMPORAL DATA COMPRESSION

[75] Inventors: Bruce M. Steinhaus, Parker; Randy T. Wells, Littleton, both of Colo.

[73] Assignee: Telectronics Pacing Systems, Inc., Englewood, Colo.

[21] Appl. No.: 738,184

[22] Filed: Jul. 30, 1991

[51] Int. Cl.⁵ .............................................. A61B 5/0452
[52] U.S. Cl. ...................................... 128/702; 128/705
[58] Field of Search .................................. 128/702, 705

[56] References Cited

U.S. PATENT DOCUMENTS

| | | | |
|---|---|---|---|
| 4,202,340 | 5/1980 | Langer et al. | 128/419 D |
| 4,732,158 | 3/1988 | Sadeh | 128/702 |
| 5,000,189 | 3/1991 | Throne et al. | 128/702 |

OTHER PUBLICATIONS

D. Lin et al., "Identification of Ventricular Tachycardia Using Intracavitary Ventricular Electrograms: Analysis of Time and Frequency Domain Patterns", *PACE*, vol. 11, pp. 1592–1606 (1988).

B. M. Steinhaus et al., "Detection of Ventricular Tachycardia Using Scanning Correlation Analysis", *PACE*, vol. 13, pp. 1930–1936. (Dec. 1990, Part II).

*Primary Examiner*—William E. Kamm
*Assistant Examiner*—Scott M. Getzow
*Attorney, Agent, or Firm*—Gottlieb, Rackman & Rackman

[57] ABSTRACT

A method and apparatus for detecting cardiac arrhythmias in a patient's heart is disclosed. The monitoring method and apparatus sense cardiac electrical signals when the heart is functioning in a known cardiac state, then characterize this known cardiac state by storing a temporally compressed template of time sequence samples. The method and apparatus allow testing during multiple different cardiac states and provide for storage of templates associated with each state. Subsequently, when the heart is functioning in an unknown cardiac state, the method and apparatus monitor cardiac electrical signals by temporally compressing samples and scan correlating these samples with the previously stored template sequences to derive correlation coefficients. The method and apparatus then use these correlation coefficients to characterize cardiac function.

28 Claims, 8 Drawing Sheets

FIG. 5B.
TEMPLATE — NSR (1000Hz)
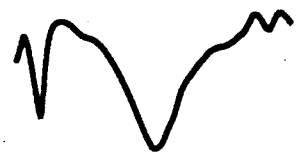
FIG. 5A.
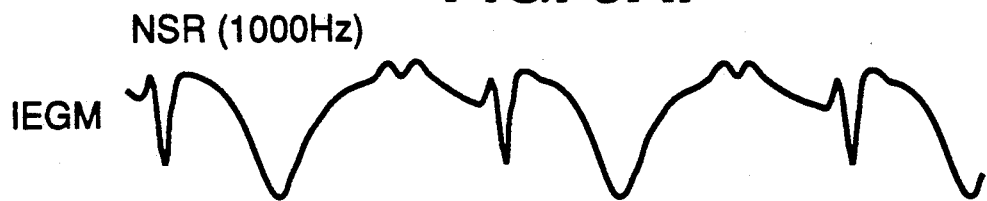
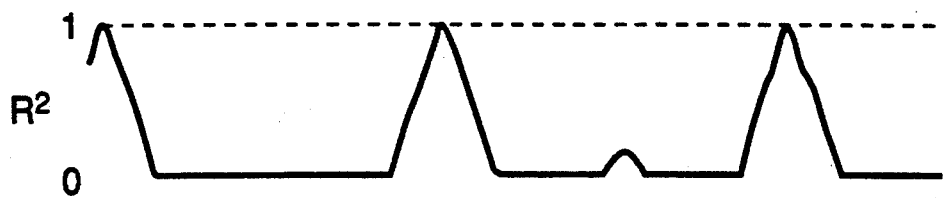
FIG. 5C.

FIG. 5E.
TEMPLATE — NSR (50Hz)
FIG. 5D.
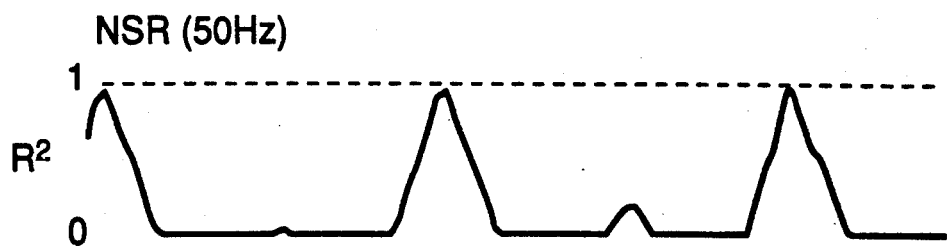
FIG. 5F.

FIG. 7A.
TEMPLATE — NSR
FIG. 7B.
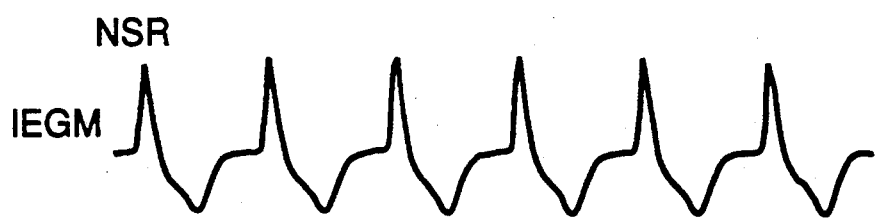
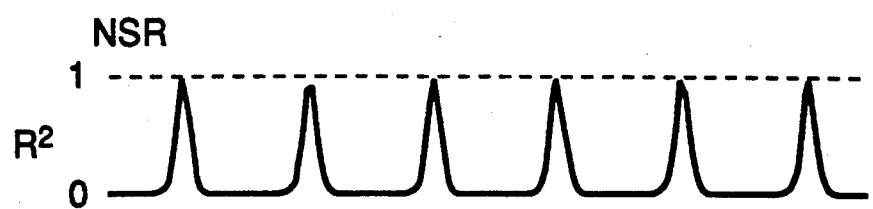
FIG. 7C.

FIG. 7D.
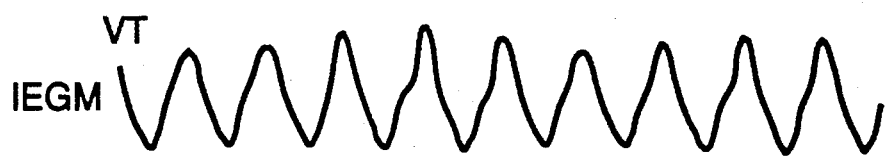
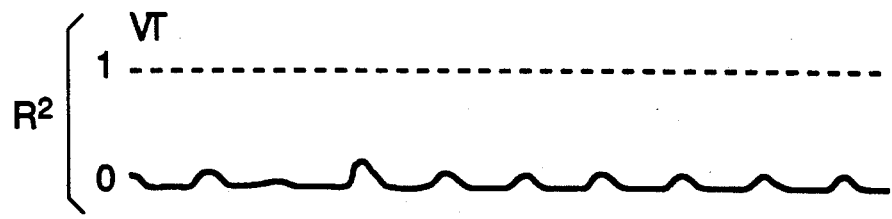
FIG. 7E.

DETECTION OF CARDIAC ARRHYTHMIAS USING CORRELATION OF A CARDIAC ELECTRICAL SIGNALS AND TEMPORAL DATA COMPRESSION

TECHNICAL FIELD

This invention relates generally to cardiac control and monitoring devices, including implantable pacemakers, arrhythmia control systems and defibrillators, and more particularly to systems within such devices which, to detect cardiac arrhythmias, perform signal processing and analysis in a manner which reduces the number of individual computations required and thereby reduces energy requirements.

BACKGROUND OF THE INVENTION

An implantable medical apparatus which executes cardiovascular control operations may evaluate cardiac electrical signals for many purposes. A cardiac control instrument analyzes cardiac signals to determine how well the cardiovascular system is performing. As a result of this analysis, the instrument responds to the detection of a predetermined criteria by automatically initiating control operations. One class of signal analyzers examines the time sequence of cardiac signal amplitudes to detect changes in the morphology, or shape, of the cardiac waveform which are indicative of cardiac function.

Most common cardiac control devices, including cardiac pacemakers, employ a rudimentary form of signal morphology analysis. These devices sense the amplitude of intracardiac electrogram signals and compare the instantaneous sensed amplitude to a preset threshold value. If the signal amplitude is larger than the threshold, the pacemaker inhibits its pacing stimulus generation response. Noise, including cardiac signals arising from sources other than those intended for measurement, adversely influences this simple control mechanism.

More sophisticated morphology analysis techniques are required for controlling other, more complex, diagnostic and therapeutic operations. One example of a function requiring a sophisticated analysis technique is the reliable detection of cardiac arrhythmias. The difficult problem of cardiac arrhythmia detection, including detection of ventricular tachycardia and fibrillation, has been addressed using many cardiac signal morphology procedures. One effective procedure, as proven in tests involving both intracardiac signal and surface electrocardiograms and reported by D. Lin et al. in "Identification of Ventricular Tachycardia Using Intracavitary Ventricular Electrograms: Analysis of Time and Frequency Domain Patterns", PACE, Vol. 11, pages 1592-1606 (1988), is the correlation of the detected signal with a previously recorded signal waveform which is known to characterize a particular diagnostic condition. Correlation is the summation of the products of point-by-point multiplications of two waveform sequences for the purpose of deriving a standard of similarity between the two waveform sequences. Unfortunately, correlation analysis requires such computational complexity that it is impractical in an implanted device. Because the device expends energy on each computational step and correlation requires so many computations, the lifetime of an implanted device performing correlation would be unreasonably short or the battery size too large for practical usage.

In many cardiac arrhythmia patients, there is a critical need for a reliable method for differentiating sinus rhythm from ventricular tachycardia (VT). If a cardiac control device had the capability of distinguishing sinus rhythm from VT, it could monitor heart activity to determine whether there was a need to perform a procedure for terminating heart disorders or arrhythmias. (This procedure is called cardioversion). Most early methods for differentiating sinus rhythm from VT were based on analyzing the timing between consecutive R-waves within a sensed electrocardiogram. Diagnostic devices would determine the R-wave rate and compare it to a predetermined maximum rate of sinus tachycardia. Some devices would also analyze the rate stability of the heart and the quickness of the onset of rate changes. Because these rate change characteristics of the R-wave always accompany ventricular tachycardias, a device controlled by these procedures will consistently detect and respond to such arrhythmias. Unfortunately, a normally functioning heart also may exhibit these rate change characteristics. For example, such rate changes may indicate only that the patient is exercising. Therefore, in addition to monitoring the rate, it is beneficial for a device to analyze the morphology of cardiac signals.

Langer et al., in U.S. Pat. No. 4,202,340, entitled "Method and Apparatus for Monitoring Heart Activity, Detecting Abnormalities, and Cardioverting a Malfunctioning Heart", issued May 13, 1980, describe an antitachycardia pacing system which detects arrhythmias by analyzing the morphology of cardiac signals. The arrhythmia detection system of the Langer et al. invention analyzes cardiac signal morphology statistically by developing a probability density function, which compares the amplitudes and locations of points in an analyzed cardiac waveform with the expected locations of points of a predetermined "normal" waveform. When the waveform becomes irregular, as measured by the probability density function, this indicates an abnormal cardiac function. The probability density function defines the fraction of time, on the average, that a signal spends between two amplitude limits. The basis for decision in this process is that the amount of time spent at baseline in each cardiac cycle is significantly longer during sinus rhythm than during ventricular tachycardia or ventricular fibrillation. The probability density function is the measure of time the signal spends away from the isoelectric baseline. It is markedly different during ventricular fibrillation than it is during normal sinus rhythm. The probability density function detects ventricular fibrillation (VF) reliably since the signal is seldom near the isoelectric line during VF. However, the probability density function is not nearly as reliable for detecting ventricular tachycardia.

The probability density function approach to arrhythmia detection is often unreliable because, if the predetermined "normal" waveform is not properly synchronized with the analyzed waveform, the device may incorrectly classify a waveform as a fibrillation condition upon the occurrence of some forms of high rate, or even low rate, ventricular tachycardia, in addition to true ventricular fibrillation. A particular problem occurs in the presence of ventricular conduction abnormalities. Defibrillation which is triggered by a high rate tachycardia is acceptable because high rate tachycardia can be fatal if it occurs at an elevated rate so considerable that not enough blood is pumped to sustain the body. However, generating defibrillation pulses in the event of low rate, non-life threatening tachycardia is inappropriate and possibly harmful.

Correlation analysis of intra-cavitary ventricular electrograms is another technique for analyzing cardiac waveform morphology which improves specificity of arrhythmia recognition. Correlation waveform analysis is a reliable technique for discriminating ventricular tachycardia from sinus rhythm. It has been used for over two decades in the analysis of surface lead morphology as well as for analyzing esophageal electrograms, intra-ventricular electrograms and intra-atrial electrograms. While correlation analysis is effective, it requires a waveform sampling rate of about 1 kHz to properly distinguish arrhythmia waveforms. Furthermore, the number of computations it requires is too demanding for usage in the low energy environment of an implantable device.

One modified technique for performing standard correlation is by multiplying the waveform sequences in a section-by section manner called piecewise correlation analysis, which provides for a reduction in the number of required computations by limiting the correlation procedure to operate only in the vicinity of the R-wave. In one example of piecewise correlation, a signal processing system defines a representative "normal" signal by measuring a ventricular electrogram signal template when the heart is functioning with a normal sinus rhythm. The system specifies this template by "windowing" the waveform, detecting the QRS complex of the cardiac signal and storing a predetermined number of samples before and after the QRS complex. For example, a waveform window may include 64 samples, which contain the QRS complex and are acquired at a 1000 Hz rate. The system averages a number of these waveform window for a preset number of cardiac cycles with the QRS complex for each cardiac cycle occurring at the same sample location within the window. After sampling and storing the template waveform, the system samples the ventricular electrogram at the same rate and for the same number of samples as was done when acquiring the template samples. The device correlates these samples with the average sinus rhythm template on a beat-by-beat basis.

To provide accurate detection of ventricular tachycardia, the piecewise correlation technique requires that the QRS complexes of the template and the sample electrogram are aligned. In piecewise correlation analysis, accurate template alignment is very important to successfully distinguish ventricular tachycardia from normal sinus rhythm or atrial fibrillation. In practice, alignment errors greater than four to five milliseconds cause a large and unpredictable variability in correlator results. Furthermore, alignment errors frequently are not recognized since a sensing determination aligned on some feature other than the R-wave may still result in a high correlation output.

Reliable template alignment is not a simple procedure. For example, a system which aligns R-waves according to a measured point of maximum intracardiac electrogram (IEGM) amplitude or corresponding to the peak derivative of the signal does not provide adequate alignment due to the large variability in amplitude and slope of the signal waveform. Signal processing of the cardiac signal to clarify the position of the R-wave using a variety of search windows and filtering techniques is helpful for particular signal morphologies but no single alignment procedure is adequate for all patients. The wide variability in cardiac signal morphologies for different patients and also for different times for the same patient cause these alignment difficulties.

Furthermore, a system which performs window alignment based on the peak cardiac signal amplitude is susceptible to errors from T-wave sensing. Occasional patients may display T-waves which are consistently larger in amplitude than R-waves. Consequently, windows may align on the T-wave or may align on the R- and T-waves in alternating cardiac cycles. Systems which align the template and sample signals based on the location of the sensed peak derivative commonly err from five to ten milliseconds because of the noisy nature of derivative signals. When combined with low pass filtering, alignment by peak derivative sensing improves somewhat but remains unacceptable.

The small size of the piecewise correlation window which is necessary to provide the computational efficiency for an implantable device leads to an additional source of alignment error. As the device performs piecewise correlation over a single cardiac cycle it may detect multiple peaks, possibly caused by T-wave sensing or detection of multiple peaks associated with the R-wave.

Full scanning correlation, in which a continuously sampled cardiac signal is correlated with a template sequence having a predetermined length smaller than the duration of the shortest possible cardiac cycle, avoids the alignment problems inherent in piecewise correlation. Unfortunately, full scanning correlation requires an excessive number of computations, and therefore too much power drain, for an implantable device.

It is, therefore, a primary object of the present invention to provide for processing of cardiac electrical signal data in a compressed form, thereby reducing the computational and energy requirements of the apparatus.

It is a further object of the present invention to provide a low power demand device and a reliable detection circuit to accurately identify ventricular tachycardia and ventricular fibrillation.

It is an additional object of the present invention to provide a system for reliably detecting abnormal ventricular signals, based on the morphology of such signals, in which the system does not require alignment of a predetermined template signal and the cardiac electrical signal under examination.

It is a still further object of the present invention to provide a system for reducing the data storage and transmission requirements of a diagnostic test device.

Further objects and advantages of this invention will become apparent as the following description proceeds.

SUMMARY OF THE INVENTION

Briefly stated, and in accordance with one aspect of the present invention a method and apparatus for monitoring cardiac electrical signals to detect functional abnormalities, such as cardiac arrhythmias of a patient's heart, are provided in a cardiac control or monitoring system. The monitoring method and apparatus of this invention sense cardiac electrical signals when the heart is functioning in a known cardiac state, then characterize this known cardiac state by storing a temporally compressed template of time sequence samples. The method and apparatus allow testing during multiple different cardiac states and provide for storage of templates associated with each state. Subsequently, when the heart is functioning in an unknown cardiac state, the method and apparatus monitor cardiac electrical signals by temporally compressing samples and scan correlating these samples with the previously stored template sequences to derive correlation coefficients. The method and apparatus use these correlation coefficients to characterize cardiac function.

The data compression method and apparatus reduce the number of data time samples by subtracting each of a predetermined number of consecutive noncompressed samples of input cardiac electrical signal from the most recently determined compressed sample, where the predetermined number represents the compression ratio. The method and apparatus then store each of the non-compressed samples and its associated absolute difference value from each subtracting step result and mutually compare each of the stored absolute difference values to determine the largest absolute difference. The current compressed sample is set to the value of the stored noncompressed sample associated with the largest absolute difference.

In accordance with further aspects of the present invention, a cardiac control and monitoring device includes a signal processing system for detecting cardiac arrhythmias which samples cardiac signals, derives a "normal" template waveform sequence from these signals, compresses both the template sequence and subsequent cardiac signal samples, then correlates the compressed template sequence with the compressed cardiac signal sample sequence using a scanning correlation technique. A digital processing system performs data compression of the template and cardiac signal sequences using a unique and improved temporal data compressor which decimates (reduces) the signal from a sampling frequency to a compressed frequency by removing X of every Y samples, saving only the sample with the maximum excursion from the last saved sample. For example, in the preferred embodiment of the invention, the compressor reduces the signal rate from 250 Hz to 50 Hz by removing four of every five samples. Temporal data compression reduces the data in terms of time rather than amplitude.

The procedure for temporally compressing the template and cardiac signal sequences is simple and efficient, requiring few computations for each input sample, and provides for conservation energy by reducing the total number of computational steps per cardiac cycle. Despite the reduction in data volume, this compression method maintains the accurate temporal, amplitude, and morphology information contained within the original cardiac signal.

In addition, this compression procedure permits "a priori" specification of the compression factor and, therefore, the computation requirements. The distinctive data compression scheme conserves information by preserving, respectively, uniform input and output sampling periods and the major amplitude changes in the original data during the rapid deflections of the QRS complex. The compression procedure is simple to implement, executes in real-time on most or all processors for signals with a bandwidth standard in cardiology applications, and provides for large compression ratios while preserving the fidelity of peak amplitude variations and waveform morphology in cardiac signals. By preserving peak amplitude variations within the compression period the procedure has no inherent low pass filter effect (at the expense of retaining large amplitude noise spikes). Data compressing in this nonlinear manner appears to avoid the Nyquist sampling limitations (at the expense of a slight temporal phase shift in the output data).

The uniform sampling period, which is inherent in the data compressor of the present invention, is advantageous because it requires no special decoding algorithm prior to restoring the signal for processing or display.

Signal processors outside the field of cardiac control and monitoring devices normally perform data compression to reduce data storage and transmission requirements rather than to limit the number of computations in determining a correlation function.

The key to reducing computations in scanned correlation is to temporally compress the template and input waveforms before performing the correlation computation. To perform a correlation computation requires TX multiplications per second where T is the number of samples in the template and X is the sample rate of the cardiac signal. The number of multiplications increases with the square of the sample rate. By compressing the template and sample cardiac signal each by a factor of 5, the necessary number of multiplications decreases by a factor of 25. The data compression technique of the present invention provides for compression ratios of 20:1, thereby dramatically reducing the number of necessary computations, while yielding results after correlation which are nearly identical to results produced by the correlation of signals which have not been compressed.

The scanning compressed correlation method of this invention is optimized for computational efficiency and is an accurate and reliable method for distinguishing normal sinus rhythm from ventricular arrhythmias. The combination of data compression and full scanning correlation provides a reliable detector of ventricular tachycardia which is easily implemented in an antitachycardia device. A data compression procedure is normally utilized to reduce data storage requirements of an apparatus. In the present invention, the purpose of data compression is to reduce computational requirements and conserve the energy expenditure of an implantable device to more efficiently use the limited battery life.

The primary motivation for providing a computationally efficient correlation procedure and apparatus is to address the need for a reliable method of differentiating sinus rhythm from ventricular tachycardia (VT). The present invention significantly reduces the number of computations necessary for performing correlation while retaining correlation's benefits of reliability and effectiveness in distinguishing VT from physiological heart function. The system must provide for a reduction in the number of computations necessary for performing sophisticated signal morphology analysis procedures to a level allowing practical implementation in an implantable device.

A secondary benefit of the invention is the reduction of storage capacity requirements. A diagnostic cardiac instrument records information contained within the cardiac signal for analysis by a health professional. It may telemeter the data to an external, non-implantable device for diagnostic purposes and it may store data representative of the ECG in a memory for subsequent analysis or telemetry. Because the intracardiac waveform normally varies little from cycle to cycle, even for patients with abnormal hearts, an efficient correlation analysis procedure provides a means for storing only a single copy of most waveforms and a record of the timing of each of these waveforms. This procedure reduces storage memory requirements significantly.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIGS. 5A, 5B, 5C, 5D, 5E, and 5F are sample illustrations of signal waveforms acted upon or produced at different stages of processing by the compressed correlation processor of the present invention, in which FIG. 5A is a 1000 Hz normal sinus rhythm cardiac signal, FIG. 5B is a 1000 Hz normal sinus rhythm template, FIG. 5C is a 1000 Hz correlation result, FIG. 5D is a compressed 50 Hz normal sinus rhythm cardiac signal, FIG. 5E is a compressed 50 Hz normal sinus rhythm template, and FIG. 5F is a compressed 50 Hz correlation result;

FIGS. 7A, 7B, 7C, 7D, and 7E are sample illustrations of signal waveforms indicating two examples of cardiac behavior, normal sinus rhythm and ventricular tachycardia, in which FIG. 7A is a normal sinus rhythm template, FIG. 7B is a normal sinus rhythm signal, FIG. 7C is a normal sinus rhythm correlation result, FIG. 7D is a ventricular tachycardia signal, and FIG. 7E is a ventricular tachycardia correlation result.

DETAILED DESCRIPTION

Figure 1:
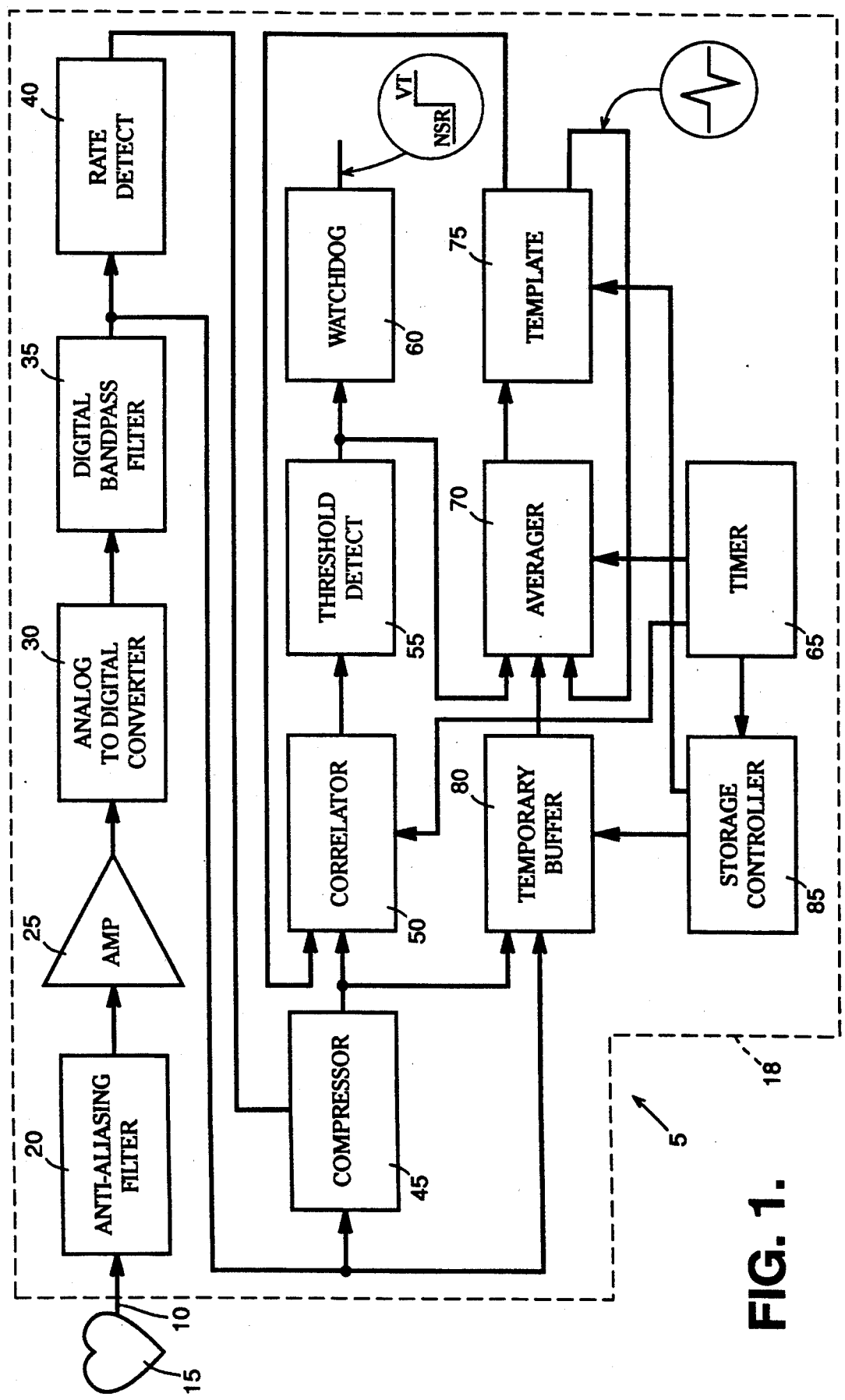
FIG. 1 is a block diagram of a preferred embodiment of the invention, in which a digital scanning correlator operates as a ventricular tachycardia detector.

Only those parts of a cardiac control or diagnostic instrument which are necessary for an understanding of the present invention are shown in the drawings. Thus, although useable in a cardioverter/defibrillator for example, the arrhythmia reversion mechanism of the latter is not shown.

FIG. 1 illustrates a preferred embodiment of a digital scanning correlator, shown generally at 5, in accordance with the present invention. This figure exemplifies the usage of the scanning correlator as the basic control element in a system for detecting ventricular tachycardias by sampling electrocardiograms and comparing the sampled signals with stored signals composed of average or normal sinus rhythm waveforms. Cardiac heart beat signals are sensed by electrodes (not shown) in the ventricle of the heart 15. The electrodes are electrically connected to leads 10 which in turn extend to digital correlator electronics contained within a case 18. The scanning correlator 5 detects cardiac signals using one of the configurations standard in cardiac pacing: bipolar, unipolar tip-case or unipolar ring-case. Unipolar signals, arising from cardiac potentials accumulated over a larger surface of the ventricle, generally contain more information than bipolar signals, providing a more reliable correlation result. On the other hand, bipolar signals offer better rejection of muscle and motion artifacts and noise, and provide the most detailed signal description of the electrophysiological state from a localized region of the ventricle.

The signal on the leads 10 is input to a low pass anti-aliasing filter 20 with a maximum high frequency cutoff of about 125 Hz. In the field of signal processing, the sampling theorem states that an analog signal, such as the signal applied to the anti-aliasing filter 20, is uniquely described by a set of uniformly spaced discrete (digital) samples taken at a particular sampling frequency, as long as no signal energy exists at frequencies greater than or equal to half this sampling frequency. The frequency of half the sampling frequency is called the "folding frequency" because signals containing energy components at frequencies higher than the folding frequency, when sampled at the sampling frequency, will contribute a noise component to a reconstructed signal at the sampling frequency less the signal frequency. This noise is called aliasing noise. The high frequency cutoff (125 Hz) of the anti-aliasing filter is selected to correspond to a folding frequency appropriate for a sampling frequency of 250 Hz. Although the antialiasing filter cutoff is chosen to correspond to the folding frequency in the preferred embodiment of the invention, a cutoff frequency ranging down to 25 Hz or lower is prudent for practical filter designs.

The filtered signal passes through a unity gain amplifier 25 to an analog to digital converter 30 which digitizes the cardiac signal for sampling at 250 Hz. The correlator limits the frequency of the digitized cardiac signal using a digital bandpass filter 35 to attenuate signals below 0.25 and above 11 Hz to remove line frequency noise at 50 Hz or 60 Hz, while retaining essentially all of the diagnostic information contained in a cardiac signal. In the preferred embodiment of the invention, the high frequency cutoff is set to the apparently low frequency of about 11 Hz. One reason for limiting the sampled signal to this range is to eliminate or reduce artifacts arising from the aliasing of line frequency noise into the desired signal. Although the original signal is sampled at a frequency of 250 Hz, data compression reduces the effective frequency to 50 Hz. Therefore, the high frequency cutoff is set lower than the effective folding frequency of 25 Hz (half the effective sampling frequency). A cutoff frequency as low as 11 Hz prevents aliasing in filtering circuits having common attenuation characteristics to yield an appropriately small output at 25 Hz.

A signal correlator must perform many computations when calculating a single correlation coefficient. The service lifetime of an implantable device is inversely proportional to numerical processing it must perform. A rate detect block 40 controls whether the correlator is active at a given time. This embodiment of the invention detects when the heart is in ventricular tachycardia as opposed to normal sinus rhythm. Since ventricular tachycardia only occurs when the heart is beating at a high rate (although a high rate does not guarantee the tachycardia condition), correlation to analyze cardiac signal morphology is not necessary unless the heart rate is high. Rate detect block 40 determines the current heart rate and compares it to a predetermined analysis threshold rate. Normally if the rate is below the threshold, the rate detect block disables the correlation function. Periodically (about once per day), the digital correlator should update the correlation template. While updating the correlation template, the rate detect block 40 controls the operations of the correlator in a manner opposite to its operation while performing scanning correlation. During template updating, the rate detect block 40 prevents contamination of the template waveform with nonstandard cardiac rhythms by disabling the correlator when the cardiac rate is high. Only if the rate is characteristic of normal sinus rhythms does the rate detect block enable the correlator to update the template.

The 250 Hz samples of digitized cardiac signal pass from the bandpass filter 35 to a compressor 45, and selectively to a temporary buffer 80 if the latter is enabled by a storage controller 85. Scanning correlation processing requires a number of computations, which number is approximately proportional to the square of the sample rate for both the input data and the correlation template, motivating a reduction in effective sampling rate as much as possible. The amount of possible reduction in effective sampling rate depends on the highest frequency content of the signal. For cardiac waveforms using the described compression method, compression to 50 Hz produces an accurate signal for analysis and storage. The temporal data compressor eliminates four of every five samples, saving from each group of five samples only the sample with the maximum excursion from the last saved sample, to decimate or reduce the signal from a frequency of 250 Hz to 50 Hz.

The data compression procedure of block 45 analyzes a predetermined number of input samples to find the value of the sample having the maximum excursion, positive or negative, from the most recent output sample. The predetermined number of input samples for each output sample is the compression ratio. The output has a uniform sample period because a fixed number of input samples are evaluated for each of the output samples.

Figure 2:
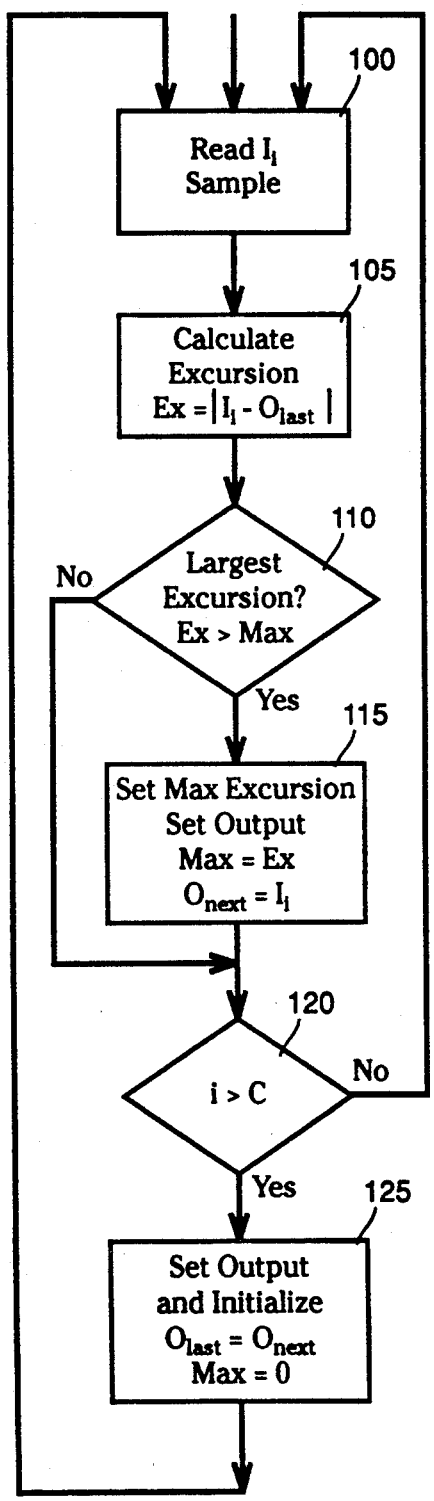
FIG. 2 is a flow chart illustrating the operational steps for one example of the data compression procedure.

FIG. 2 illustrates one embodiment of the data compression procedure. In block 100, the compressor reads the input data sample $I_i$, beginning with the first sample (i=1). In block 105, the compressor calculates the excursion, Ex, from the output data sample from the last iteration of the procedure $O_{last}$, according to Equation (1) below:

$$Ex = |I_i - O_{last}|. \qquad (1)$$

If the excursion, Ex, is greater than the maximum excursion, Max, in block 110, then the compressor (in block 115) sets the value of Max to Ex and temporarily stores the input sample, $I_i$, in a memory location for the next output data sample, $O_{next}$. Following this, or if the excursion Ex is less than the maximum excursion Max in block 110, the procedure returns via block 120 to block 100 to perform blocks 100 to 115 in a loop C times, where C is the compression ratio. After looping C times, as controlled by logic block 120, the compressor returns the result, $O_{next}$, to the calling procedure and sets the value of $O_{last}$ to $O_{next}$ to prepare for compression of the next sample in block 125.

Figure 3:
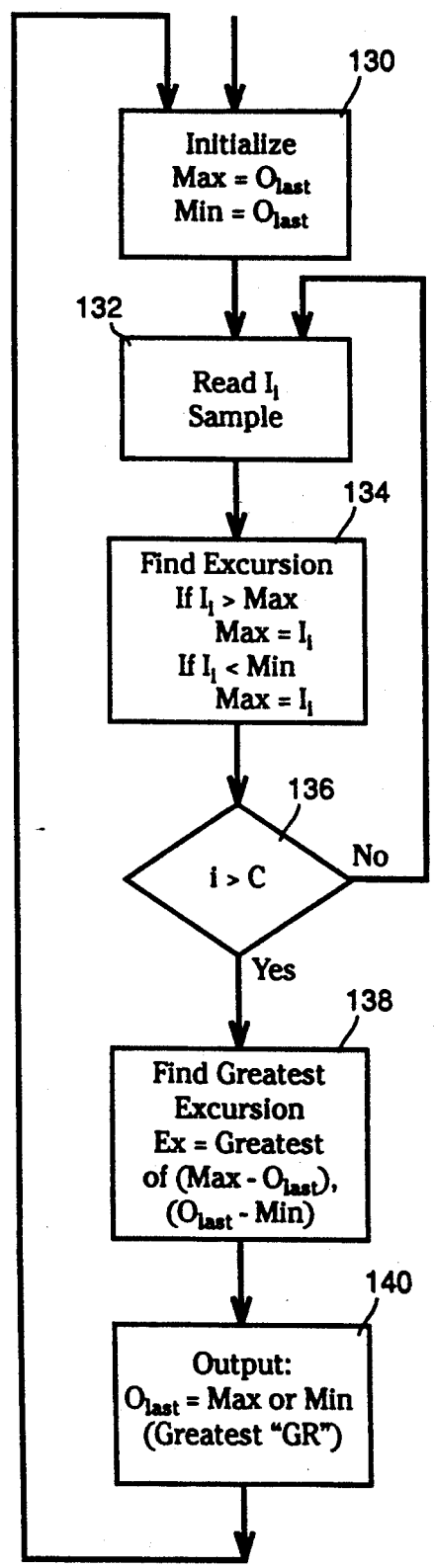
FIG. 3 is a flow chart illustrating the operational steps for a second example of the data compression procedure.

FIG. 3 illustrates a second embodiment of the data compression procedure which is more efficient in conserving the number of computing steps for some microprocessors or controllers because it avoids the absolute value determination and subtraction within the searching loop. In block 130, the compressor sets both the maximum sample, Max, and the minimum sample, Min, to the value of the output data sample from the last iteration of the procedure, $O_{last}$. The procedure enters the test loop beginning in block 132. The procedure performs blocks 132 to 136 within the loop C times as controlled by the logic test in block 136, where C is the compression ratio. Within the loop in block 132, the compressor accesses the input data sample, $I_i$, beginning with the first sample (i=1). In block 134, the procedure updates the maximum and minimum sample values by comparing $I_i$ to Max and Min. For a given sample I at time i, if Max is less than $I_i$, it is set to $I_i$. If Min is greater than $I_i$, it is set to $I_i$. After looping C times, in block 138 the compressor determines the positive and negative excursions, respectively, by subtracting $O_{last}$ from Max and by subtracting Min from $O_{last}$. The compressor stores the greater of the positive and negative excursions in $O_{last}$ to prepare for compression of the next sample and returns this value as the compressor result to the calling procedure in block 140.

Data compression to 50 samples per second (20 msec sample period) using this procedure preserves the majority of the information content of intracardiogram data. Data compression to 25 samples per second or less results in visual degradation of the signal including the loss of temporal resolution less than the sampling period, temporal (phase) shift in the output data, and temporal widening of fast events (QRS complex).

Again referring to FIG. 1, when a 5 to 1 compression ratio is utilized, the compressor output of block 45 is a 50 Hz digital signal which passes to a correlator 50 and possibly to temporary buffer 80, if the latter is enabled by storage controller 85. Temporary buffer 80 and storage controller 85 provide for the storage of compressed or non-compressed waveforms for some scanning compressed correlator applications. The correlator 50 correlates the input signal with a template segment of previously sampled and averaged normal sinus rhythm waveform data (NSR).

The standard correlation formula is shown in Equation (2), below:

$$R = \frac{\sum_{i=0}^{N}(T_i - \mu_T)(X_i - \mu_X)}{\sqrt{\sum_{i=0}^{N}(T_i - \mu_T)^2 \sum_{i=0}^{N}(X_i - \mu_X)^2}} \qquad (2)$$

where R is the correlator result for each data sample, each T is a template sample at time i, X is the cardiac signal sample, $\mu_T$ and $\mu_X$ are the means for the template samples T and the cardiac signal samples X, respectively, and N is the template length. Standard correlation requires a square root operation in the denominator of the equation, which though possible, would be difficult to implement in an implantable device. Rather than performing the square root operation, the preferred embodiment of the invention squares the numerator and denominator of the right side of the equation, eliminating the square root operation, leaves the left side correlation result R in its squared form $R^2$, and uses this squared form, termed "correlation coefficient," as a surrogate for the standard result. By avoiding the computationally-intensive square root operation at the cost of only one additional multiplication operation, the squaring of the numerator of the right hand side of the equation, this method of analysis promotes efficiency and power conservation. Since the correlation coefficient $R^2$ is the squared form of the correlation result R, it always takes a positive value.

Standard correlation requires the determination of the means, $\mu$, for both the template, T, and cardiac signal, X, samples. The preferred embodiment of the invention eliminates the correction for the mean since high pass filtering within the aforementioned bandpass filter substantially removes the DC component of the signal, forcing the mean to zero. By removing the mean correction, this technique saves N subtraction operations (where N is the template length) for each sample in the input waveform, X, and simplifies the computation for each sample. Note that this simplification is only possible when the length of the template is not too small in relationship to the cardiac cycle length. For this reason, the correlator within the preferred embodiment of the invention monitors the heart rate and does not allow template lengths shorter than about 10% of the minimum cardiac cycle length.

These two simplifications change the correlation function for calculating a new correlation coefficient, $R^2$, as shown in Equation (3), below:

$$R^2 = \frac{\left(\sum_{i=0}^{N} T_i X_i\right)^2}{\sum_{i=0}^{N} T_i^2 \sum_{i=0}^{N} X_i^2}. \tag{3}$$

Figure 4:
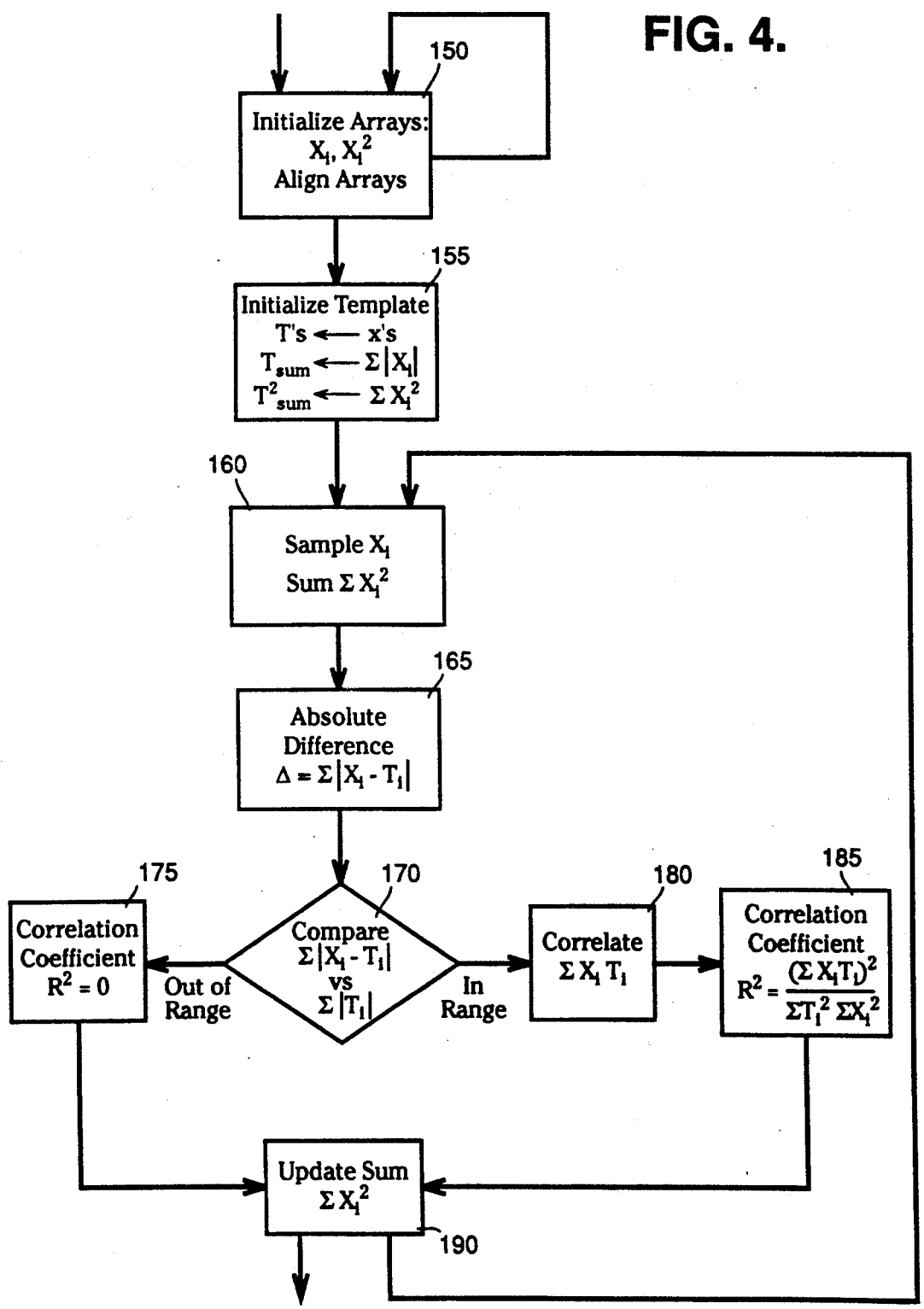
FIG. 4 is a flow chart illustrating the operational steps for the preferred embodiment of the correlator procedure.

The flowchart in FIG. 4 describes the operations performed by the correlator. Before beginning the correlation function, the correlator first initializes the cardiac signal sample arrays, X and X squared, and the scalar value of the sum of X squared over the most recent N samples. In the initialization operation, each element of each array is set to zero, as is the scalar sum of X squared. The size of the X and X squared sample arrays is based on the expected number of 250 Hz samples for a sampled interval within a cardiac cycle of normal duration. For example, a common size for X and X squared arrays for normal sinus rhythm cardiac signals may be defined to include 80% of a typical resting heart rate escape interval, a duration of approximately 700 milliseconds. Therefore, a sample rate of 250 Hz, which is temporarily compressed to 50 Hz has a compressed sample corresponding to each 20 millisecond interval. There are 35 compressed samples for each 700 millisecond array duration. If each sample is stored in a single eight bit byte, each array X and X squared is stored in 35 bytes. The size of the template array, T, matches that of arrays X and X squared.

Block 150 is a cardiac signal sampling loop which initializes the arrays necessary for correlation processing and aligns the signal waveform within the arrays to affirm that the R-wave of the cardiac signal is within the template. Within the loop, the correlator samples cardiac signal data at 250 Hz, discards four of five samples according to the data compression procedure, stores the remaining data sample in the X array, squares the sample and stores the result in the X squared array. Block 155 performs the second initialization step of storing the template selected in sampling block 150 in the template array (T). Block 155 also determines the sum of the elements in the array T squared and stores the result as a scalar parameter, the sum of T squared for N template samples. The correlator derives these data during template formation in initialization, and maintains template validity against physiological changes over time by periodic updates.

The correlator in one embodiment of the invention establishes the template length to be 80% of the average normal sinus rhythm cardiac cycle length. Alternatively, the correlator may utilize a variable template length, which is set according to the purpose and application of the scanning correlator. In general, long templates allow better discrimination between ventricular tachycardia and normal sinus rhythm signals. Short templates allow the correlator to function properly over a wide range of heart rates. In contrast, correlating a signal with a long template will give rise to errors when the signal heart rate is high enough so that the interval between heartbeats is shorter than the template. In addition, short templates are advantageous for discriminating between ventricular tachycardias and supra-ventricular tachyardias.

Ventricular tachycardia is a pathological heart condition under which the heart fails to supply blood to the body and which may lead to fibrillation and sudden death. Supra-ventricular tachycardia is a high heart rate indicative of exercise or stress and does not indicate an abnormal action of the heart. Since the heartbeat rate varies greatly over time, it is desirable for the template length to vary accordingly. One method of dynamically varying the template length is to truncate the template length when the heart rate interval is shorter than the stored template length. The correlator performs truncation by determining the maximum number of template array samples corresponding to the heart rate interval (the time interval for the current heart rate) measured in rate detect block 40 (of FIG. 1). The correlator will determine the correlation coefficient ($R^2$) for no more than this maximum number, ignoring additional template samples.

The fact that the electrocardiogram QT-interval varies in a manner nearly proportional to the heart rate interval gives rise to a second method of dynamically changing the template length. Before performing the correlation operation, the device decimates the template array by a factor inversely proportional to the heart rate interval determined in rate detect block 40 (of FIG. 1). If the correlator uses this method (i.e., decreasing the decimation or compression factor as the heart rate interval increases, and vice versa) for varying the template length, initialization of the template in blocks 150 and 155 of FIG. 4 involves acquisition of the template prior to data compression thereof, with decimating data compression occurring later, prior to correlation in block 180, to provide the most accurate template construction. Similar template accuracy is possible if the device saves a number of templates in block 155 of FIG. 4, determined using different decimation factors (corresponding to various heart rates). When performing the correlation in block 180 of FIG. 4, the correlator selects the appropriate template according to the heart rate determined in rate detect block 40 of FIG. 1.

The correlation coefficient, $R^2$, is normally independent of the cardiac signal amplitude because the sum of the X squared factors appears in both the numerator and the denominator of the correlation equation, as may be seen in Equation (3), above. Therefore, it is possible that correlation of noise in the cardiac signal or, more importantly, correlation of random nonphysiological signals in the cardiac signal, with the template can result in a large correlation coefficient. These random nonphysiological signals are low level signals which may correlate highly with the template due to the statistical nature of the correlation operation, but are not considered to be physiological signals.

The correlator includes an absolute difference measurement to detect and respond to these nonphysiological signals. For each sample, X, the correlator determines the absolute value of the difference between the cardiac signal sample and the template sample. The correlator then sums the difference magnitudes for the entire sample length, N, to determine the nonphysiological signal measurement for the current cardiac cycle.

To determine the relationship of the nonphysiological signal magnitude to the signal, the correlator compares the nonphysiological signal value to a normalization parameter, $T_{norm}$. The normalization parameter is chosen to be the sum of the absolute values of the template samples for the length of the template because this averaged value of normal samples best approximates the expected signal magnitudes in the absence of nonphysiological signals. While initializing the template in block 155, the correlator determines the absolute value for each sample, T, and sums each value to create the normalization parameter, $T_{norm}$, as shown in Equation (4), below:

$$T_{norm} = \sum_{i=0}^{N} |T_i|. \tag{4}$$

After initialization, control passes to block 160 which begins the cardiac signal sampling for correlation determination. To conserve energy in an implantable device, the preferred embodiment of the invention only performs the correlation function when necessary. For a device functioning as a cardiac arrhythmia detector, the correlation process pauses until the intrinsic cardiac rate is high enough to indicate the possibility of ventricular tachycardia or fibrillation. Other detectors which determine hemodynamic function, including cardiac output or contractility sensors, may activate the correlator. The correlator preferably maintains all parameters and arrays while the function is inactive.

In block 160, the correlator samples the data compressed cardiac signal and stores the result in X. The correlator also updates the X squared array and sum by squaring the cardiac signal sample and adding it to the scalar sum of X squared taken from a memory location.

In block 165, the correlator determines the absolute difference between corresponding template and cardiac signal samples. The absolute difference determination, shown in Statement (5) below, $$\sum_{i=0}^{N} |X_i - T_i|, \tag{5}$$

takes place within a loop which sums the difference magnitudes for each corresponding sample and template pair for all the samples in the cardiac cycle.

The correlator performs the noise test in block 170 by comparing the sum of the absolute differences determined in block 165 to the normalization parameter, $T_{norm}$. If the sum of the absolute differences is too large (for example, 0.5 times the normalization parameter), the correlator determines that the system cannot determine the correlation coefficient due to the presence of excessive nonphysiological signals. In this case the correlator sets the correlation coefficient to zero in block 175. Otherwise, the correlator derives the correlation coefficient $R^2$ via blocks 180 and 185.

Assuming that the sum of the absolute differences in block 170 is within an acceptable range (i.e., the nonphysiological signal amplitude is not too large), the correlator next determines the correlation numerator product in an iterative manner for each sample in the template. Block 180 includes the correlation numerator loop calculation, wherein the correlator multiplies each element in the cardiac signal sample array, X, by the corresponding element in the previously stored template array, T, then sums these products for all N array elements.

In block 185, the correlator determines the correlation coefficient by squaring the numerator value from block 180, shown in Statement (6) below, $$\left( \sum_{i=0}^{N} ((X_i)(T_i))^2 \right), \tag{6}$$

and divides it by the product from block 160, shown in Statement (7) below, $$\sum_{i=0}^{N} (X_i)^2, \tag{7}$$

multiplied by the product from block 155, shown in Statement (8) below, $$\sum_{i=0}^{N} (T_i)^2. \tag{8}$$

In block 190, the correlator prepares for processing the next sample in block 160 by reducing the value of the memory location shown in Statement (9) below $$\sum_{i=0}^{N} (X_i)^2, \tag{9}$$

by the value of the oldest sample $X_i^2$, in the array X squared. In this manner, the correlator reduces the number of computations by maintaining the sum during sampling, then subtracting the oldest sample from the sum and adding the newest sample for each sampling cycle.

This correlation method requires N+34 multiplications, 1 division and N+5 additions per sample, i, where N is the number of samples in the template. The device may reduce computations in multiplication either by performing the correlation function in hardware, by referencing lookup tables in memory indexed by the multipliers and multiplicands or by setting the product to a minimum value if either or both the multiplier and multiplicand are too small (or negative).

Two facts allow the device to further reduce the computations for scanning correlation. First, the heart exhibits a refractory period where it is unexcitable to electrical stimuli. Secondly, the electrogram is generally a periodic waveform. A device performing operations not requiring the maximum correlator value for further processing may reduce computations by defining a refractory period following each detected heartbeat wherein the device does not measure the correlation function. A detected heartbeat, defined when the correlator output is greater than some threshold value, signals a time when the correlator can immediately cease operations. The duration of this inactive period may be set by external programming (in a device equipped with communication capabilities as known in the art of heart pacemakers).

The device may automatically and dynamically set the inactive period duration to a value inversely proportional to the measured heart rate or proportional to the template length. Alternatively, the device may trigger the inactive period using an external heartbeat identifier such as a hardware implemented high pass filter and threshold comparator similar to the sense inhibit standard in the art of cardiac pacemakers. Processing in this manner would require data storage to permit analysis of samples occurring prior to the trigger signal.

The preferred embodiment of the invention measures the correlation coefficient for the purpose of cardiac morphology analysis to detect ventricular tachycardia or fibrillation. After correlating the cardiac signal with the normal sinus rhythm template in block 50 (FIG. 1), the digital correlator compares the correlation coefficient with a predetermined threshold value in block 55. The threshold is a programmed or automatically adapting threshold value. An ideal threshold is slightly larger than the maximum correlator output value during ventricular tachycardia.

If the correlation coefficient is smaller than the threshold value, indicating a lack of similarity between the correlation coefficient and the normal sinus rhythm template and implying the occurrence of a ventricular arrhythmia, control passes to the watchdog block 60. The watchdog block 60 times the duration of the period in which the correlation coefficient is low and the cardiac rate high. If the duration is sufficiently long, the watchdog block classifies the condition as a ventricular arrhythmia and initiates a response signal. This response signal may be an input signal to a cardiac pacemaker or an antitachycardia/defibrillator device which will further respond to the signal in a manner known in the art of cardiology.

If the correlation coefficient i greater than the threshold value, showing similarity of the correlation coefficient with the normal sinus rhythm template and indicating no danger of ventricular arrhythmia, the digital correlator either becomes inactive until the rate detect block 40 again detects a high natural cardiac rate or, if timer 65 determines it is time for a periodic template update, control passes to the averager block 70.

When the rate detector 40 indicates that the heart is functioning with a normal sinus rhythm, the device periodically (timed by timer 65) updates the template waveform by detecting R-waves of consecutive cardiac cycles and determining the natural sinus rate from the interval between the R-waves in rate detect block 40, then by correlating the segments of cardiac signals in block 50, and accumulating and averaging selected segments for a predefined number of cardiac cycles in block 70. The digital correlator updates the templates only if the correlator output exceeds some threshold (for example, 0.95).

Patient morphologies may change over time due to progression of disease. These gradual changes in NSR morphology necessitate periodic updating of the template to adapt the template to the new morphology and permit reliable operation of the correlator. Normally the correlation procedure is inactive unless the correlator is sensing natural cardiac activity above a specified rate. However, the correlator must maintain a template of NSR by performing periodic template updating when the heart is functioning at normal heart rates to insure that the template does not adapt to ventricular tachycardia. The timer 65 activates the correlation procedure on the order of once per day (a reasonable interval, considering the balance between normal signal variability and power consumption requirements) when the heart is beating with normal sinus activity, to maintain the template.

When the averager 70 has accumulated the desired number of cycles, control passes to block 75 where the digital correlator stores the template by storing the averaged current X array into the T array and storing the scalar sum of X squared value into the scalar sum of T squared memory location. The number of samples in the template depends on the natural sinus rate and the duration of its associated cardiac interval. The template length is preset to a percentage (from 10% to 80%) of the average cardiac interval. The compressed correlation technique most accurately detects ventricular tachycardia when template lengths are long (up to 80% of the intrinsic interval length) because the T-wave, as well as the QRS complex, is useful in VT recognition. The correlator performs cardiac signal sampling to determine the template in a manner such that each template includes the R-wave and as much of the T-wave following the R-wave as possible since the device predicts when the next R-wave will occur from an average of cardiac intervals of recently occurring cycles and begins sampling prior to the predicted R-wave time. If an R-wave does not occur within the sampling time or if the correlation coefficient of a given sample does not meet a threshold criterion (for example 0.9), the device does not update the accumulated average.

FIGS. 5A through 5F illustrate comparisons of the results obtained by correlating cardiac signals when a cardiac electrogram and a template are not data compressed (FIGS. 5A through 5C), and when the electrogram and template are data compressed (FIGS. 5D through 5F). These comparisons are accomplished by sampling actual cardiac signal samples and performing a computer simulation of the correlation procedure. When the electrogram and template are data compressed, there is a considerable savings in the computational burden. This is afforded by the procedure of compressing the data prior to correlation using the data compression scheme of the present invention. This savings in computational burden is accomplished at the cost of only a slight degradation in the correlation coefficient.

The scanning correlation coefficient of FIG. 5C is produced by correlating a normal sinus rhythm signal (FIG. 5A) with a normal sinus rhythm template (FIG. 5B), both of which are sampled at a data rate of 1000 samples per second. The correlation procedure may be visualized by sliding the template waveform of FIG. 5B along the cardiac signal waveform of FIG. 5A. The correlation coefficient of FIG. 5C is at its maximum value at each position of the template in which the morphologies of the template waveform and the cardiac signal most closely match.

Data compression of the same cardiac signal and the identical template at a 20:1 ratio reduces the effective sampling rate to 50 samples per second. Subsequent correlation of the compressed normal sinus rhythm signal (FIG. 5D) with the compressed sinus rhythm template (FIG. 5E), yields the scanning correlation coefficient of FIG. 5F. Analysis of the compressed cardiac signal waveform of FIG. 5D indicates that the compressed data retains most of the signal morphology information contained within the original data, although there is some loss of low amplitude signal information and a small degree of temporal distortion, particularly in the vicinity of the QRS complex when fast signal changes occur. The apparent similarity between the noncompressed and compressed correlation coefficient waveforms (FIGS. 5C and 5F, respectively) illustrates the usefulness of compressed scanning correlation, considering the large savings in data storage requirements (a twenty times reduction) and computational burden (a 400 times reduction).

Figure 6:
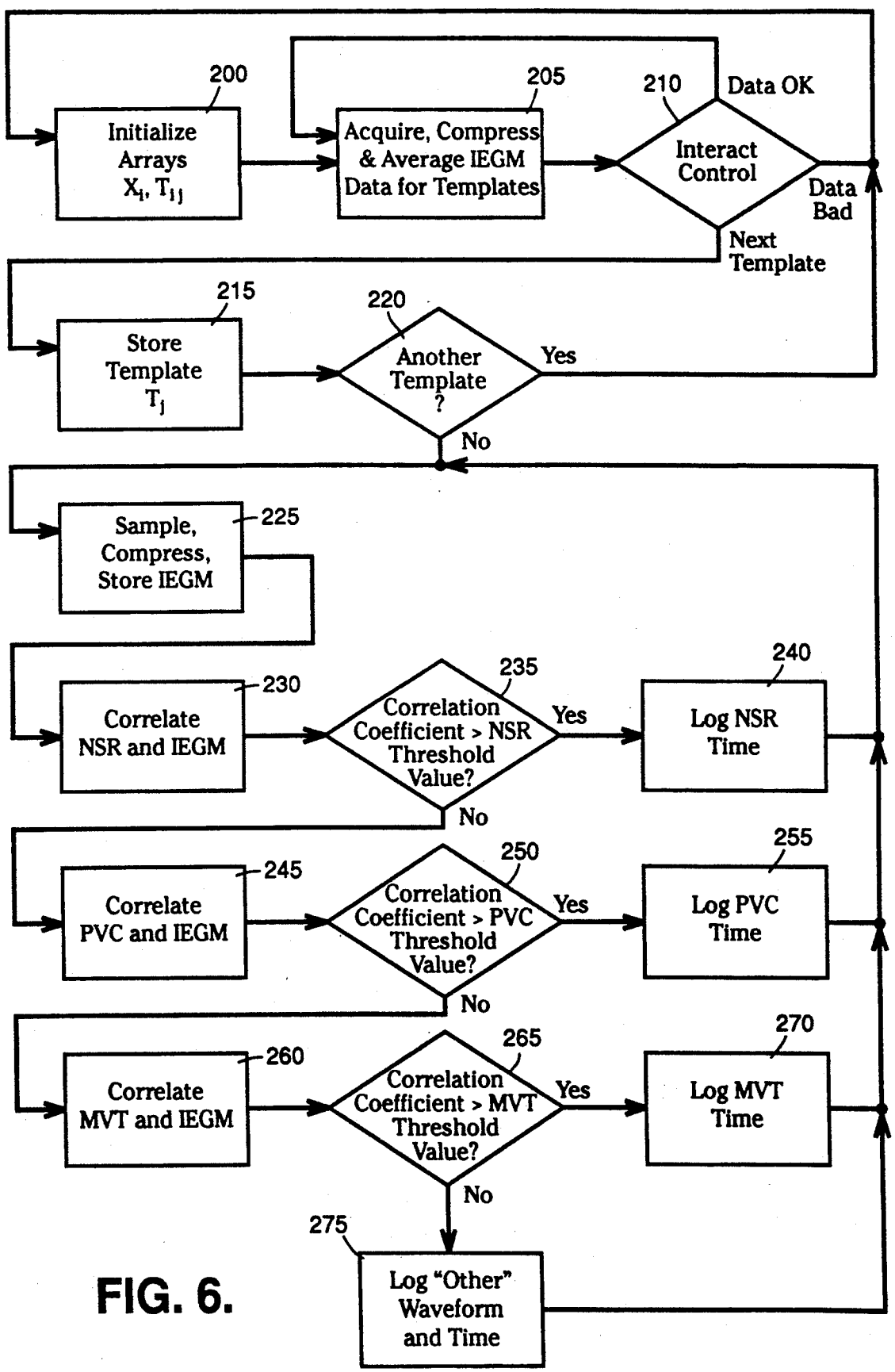
FIG. 6 is a block diagram of a digital scanning correlator operating as a data compressor.

The flow diagram of FIG. 6 illustrates the procedure for performing data reduction using the scanning correlation technique. The elements of digital correlator 5 of FIG. 1 perform the same functions both during arrhythmia detection and during data reduction applications. The digital correlator performs different functions through variations in control of the storage controller 85, timer 65 and rate detector 40 in FIG. 1.

Referring to FIG. 6, the data reduction procedure begins with initialization of data structures in block 200, which sets one template array to zero. In block 205 the digital correlator acquires, compresses and averages intracardiac electrogram data for the purpose of creating templates for one or more signal morphologies. This step will normally require interactive input from a health practitioner to associate each template with a particular type of morphology. Communication and telemetry functions which are known in the art of cardiac pacemakers permit this interaction. During a first pass through blocks 200-220, the physician will activate the digital correlator to operate in an accumulating and averaging mode to create a normal sinus rhythm (NSR) template. During this first pass through block 205, data is compressed but not correlated with a template, since no template has yet been stored. While the template is accumulating waveform data, the device transmits the sampled intracardiograms to a display device which the physician monitors (also in block 205). If a morphology other than NSR occurs, the physician can interact with the device to restart the data accumulation and averaging in block 200 as controlled by block 210. If the physician does not request termination, control passes to block 205 for more NSR averaging.

When enough NSR waveforms are compressed and averaged, according to the interactive input from the physician, control passes to logic block 215 which stores the template. The physician also can interact with the device to control logic block 220 to determine whether to accumulate and store another signal morphology. If so, control passes to block 200 which initializes a new template array. The procedure can loop through initialization steps 200 to 220 in this manner to set templates for preventricular contractions (PVC), monomorphic ventricular tachycardias (MVT), or other morphologies.

For initialization passes subsequent to the NSR (the first pass) acquisition, the accumulating and averaging block 205 performs compressed scanning correlation with the NSR template to distinguish incoming data from NSR. If the incoming signal is NSR, step 205 does not update the averaged data. During these subsequent passes the physician may force the heart to display a specific morphology by physical or chemical means, as known in the art of cardiology. As in the performance of the first loop, the physician can restart the sampling for the particular desired morphology if block 205 accumulates an undesired waveform. In a similar manner, the third and subsequent passes may include correlation with all stored templates to avoid updating a new template with waveforms having a previously set morphology.

After performing initialization in blocks 200220, the procedure begins a signal monitoring phase in block 225 which samples, data compresses and stores the intracardiac electrogram. Next, block 230 correlates the compressed intracardiogram waveform with the compressed NSR template and tests the resulting correlation coefficient with a predetermined threshold value. If the correlation coefficient is greater than the threshold, logic block 235 directs the procedure execution to block 240 which stores a short code in storage memory which identifies the time of the NSR detection. Optionally, block 240 may also periodically perform some updating of the NSR template to allow the procedure to trace gradual waveform changes. Block 240 would perform this updating procedure by averaging the current array into the template. This is accomplished by multiplying each sample in the current array by a predetermined fraction, multiplying each sample in the template array by a fraction equal to one minus the aforementioned predetermined fraction, and adding the current array to the template array. From block 240, the procedure loops back to block 225 to resume data acquisition of the waveform for a subsequent cardiac cycle.

If the NSR correlation coefficient is less than the threshold, logic block 235 passes procedure execution to block 245 which, assuming other signal morphology templates were set, correlates the compressed intracardiac waveform with another template (for example, the PVC template). Blocks 245 to 255 function in the same manner as blocks 230 to 240 to correlate the incoming data with a template, test the correlation coefficient with a threshold value, and store a code in memory to designate the time and morphology type.

FIG. 6 includes another set of blocks, 260 to 270, which perform the same operations as block triads, 230 to 240 and 245 to 255, but which correlate the incoming data with the MVT template. Another embodiment of the invention may correlate the data with more or fewer templates according to the wishes of the physician and the condition of the patient.

If no correlation result passes one of the threshold tests, the signal morphology is not known. In this case, block 275 stores the entire compressed waveform and the time of its occurrence. From each of blocks 240, 255, 270 and 275. The procedure loops back to block 225 to resume data acquisition of the waveform for a subsequent cardiac cycle.

FIGS. 7A through 7E illustrate examples of correlation coefficient results achieved, following 20:1 ratio data compression, during episodes of normal sinus rate (NSR) (FIGS. 7B and 7C) and ventricular tachycardia (VT) (FIGS. 7D and 7E). The system correlates the compressed NSR cardiac signal of FIG. 7B, and the compressed VT signal of FIG. 7D, with the compressed NSR template of FIG. 7A. The correlation coefficient resulting after correlating the template with the VT signal, illustrated in FIG. 7E, is much smaller than the correlation coefficient resulting after correlating the template with the NSR signal (FIG. 7C). A cardiac control device may analyze the value of the correlation coefficient to control a therapeutic response.

From the foregoing discussion, it is apparent that the present invention provides a signal correlation system within a cardiac control and monitoring device which accomplishes substantial improvement in conserving data storage requirements, computational burden, and energy, while providing an effective means for distinguishing normal cardiac rhythms from abnormal rhythms.

Although the invention is described with reference to a particular embodiment, it is to be understood that this embodiment is merely illustrative of the application of the principles of the invention. Numerous modifications may be made therein and other arrangements may be devised without departing from the true spirit and the scope of the invention.

What is claimed is:

1. A method of detecting cardiac arrhythmias in a patient's heart, comprising the steps of:
   sensing cardiac electrical signals when the heart is functioning in a known cardiac state;
   characterizing said known cardiac state in a time sequence of template samples;
   temporally compressing said time sequence of template samples;
   storing said temporally compressed template samples;
   monitoring a time sequence of cardiac electrical signal samples when the heart is functioning in an unknown cardiac state;
   temporally compressing said unknown cardiac state samples monitored during said time sequence;
   scan correlating said compressed unknown cardiac state samples with said stored compressed template samples to derive a correlation coefficient;
   comparing said correlation coefficient with a threshold value;
   classifying said unknown cardiac state within said known cardiac state when the correlation coefficient is greater than said threshold value, and classifying said unknown cardiac state outside said known cardiac state when the correlation coefficient is not greater than said threshold value, and
   highpass filtering said sensed cardiac electrical signals when the heart is operating in each of said known cardiac state and said unknown cardiac state to substantially eliminate the mean amplitude of each of said temporally compressed template samples and said temporally compressed unknown cardiac state samples.

2. A method according to claim 1, wherein said scan correlating step disregards the mean amplitude of each of said temporally compressed template samples and said temporally compressed unknown cardiac state samples when deriving said correlation coefficient.

3. A method according to claim 2, wherein each of said temporally compressing steps comprises the substeps of:
   subtracting each of a predetermined number of consecutive noncompressed samples of said sensed cardiac electrical signal from the most recently determined compressed sample, wherein said predetermined number is a compression ratio;
   storing each of said noncompressed samples and its associated absolute difference value from each subtracting step result;
   mutually comparing each of said stored absolute difference values to determine the largest absolute difference; and
   setting the current compressed sample to the value of the stored noncompressed sample associated with the largest absolute difference.

4. A method according to claim 3, wherein said step of characterizing said known cardiac state in a time sequence of template samples comprises the substeps of:
   sampling a first sequence of cardiac electrical signals sensed when the heart is functioning in a known cardiac state;
   storing said first sequence samples in a template memory;
   sampling and storing subsequent cardiac electrical signals;
   scan correlating said subsequent cardiac electrical signal samples with said template samples to derive a second correlation coefficient;
   comparing said second correlation coefficient with a second threshold value;
   if said second correlation coefficient is greater than said second threshold value, aligning said subsequent cardiac electrical signal samples in time;
   averaging said aligned subsequent cardiac electrical signal samples into said template; and
   repeating said sampling, storing, scan correlating, comparing, aligning, and averaging steps for a predetermined number of iterations.

5. A method according to claim 4, further comprising the steps of:
   locating an R wave in said sequence of cardiac electrical signals; and
   aligning said first sequence samples in the template memory so that the R wave sample is stored in a predetermined sample location.

6. A method according to claim 4, further comprising the steps of:
   monitoring said cardiac electrical signals to determine an intrinsic heart rate and its associated intrinsic cycle length; and
   setting a template length limit restricting the size of the template to a predetermined percentage of said intrinsic cycle length.

7. A method according to claim 6, further comprising the steps of:
   locating an R wave in said sequence of cardiac electrical signals; and
   aligning said first sequence samples in the template memory so that the R wave sample is stored in a predetermined sample location.

8. A method according to claim 6, further comprising the steps of:
   sensing cardiac electrical signals when the heart is functioning in at least one additional known cardiac state;
   characterizing said at least one additional known cardiac state in a time sequence of template samples for each additional known cardiac state;
   temporally compressing said time sequence of template samples for each additional known cardiac state;
   storing said temporally compressed template samples for each additional known cardiac state;
   scan correlating those of said compressed unknown cardiac state samples which have been classified outside said known cardiac state with said stored compressed template samples for each additional known cardiac state to derive a correlation coefficient associated with each additional known cardiac state;

mutually comparing each of said correlation coefficients with a threshold value; and classifying said unknown cardiac state within one of said additional known cardiac states according to said mutual comparison results.

9. A method according to claim 8, wherein said first mentioned known cardiac state comprises normal sinus rhythm and at least one of said additional known cardiac states comprises ventricular tachycardia.

10. A method of detecting cardiac arrhythmias in a patient's heart, comprising the steps of:

sensing cardiac electrical signals when the heart is functioning in a known cardiac state;

characterizing said known cardiac state in a time sequence of template samples;

temporally compressing said time sequence of template samples;

storing said temporally compressed template samples;

monitoring a time sequence of cardiac electrical signal samples when the heart is functioning in an unknown cardiac state;

temporally compressing said unknown cardiac state samples monitored during said time sequence;

scan correlating said compressed unknown cardiac state samples with said stored compressed template samples to derive a correlation coefficient;

comparing said correlation coefficient with a threshold value; and classifying said unknown cardiac state within said known cardiac state when the correlation coefficient is greater than said threshold value, and classifying said unknown cardiac state outside said known cardiac state when the correlation coefficient is not greater than said threshold value, wherein said step of characterizing said known cardiac state in a time sequence of template samples comprises the sub-steps of:

sampling a first sequence of cardiac electrical signals sensed when the heart is functioning in a known cardiac state;

storing said first sequence samples in a template memory;

sampling and storing subsequent cardiac electrical signals;

scan correlating said subsequent cardiac electrical signal samples with said template samples to derive a second correlation coefficient;

comparing said second correlation coefficient with a second threshold value;

if said second correlation coefficient is greater than said second threshold value, aligning said subsequent cardiac electrical signal samples in time;

averaging said aligned subsequent cardiac electrical signal samples into said template; and repeating said sampling, storing, scan correlating, comparing, aligning, and averaging steps for a predetermined number of iterations.

11. A method according to claim 10, further comprising the steps of:

monitoring said cardiac electrical signals to determine an intrinsic heart rate and its associated intrinsic cycle length; and setting a template length limit restricting the size of the template to a predetermined percentage of said intrinsic cycle length.

12. A method according to claim 11, further comprising the steps of:

locating an R wave in said sequence of cardiac electrical signals; and aligning said first sequence samples in the template memory so that the R wave sample is stored in a predetermined sample location.

13. A method according to claim 10, further comprising the steps of:

locating an R wave in said sequence of cardiac electrical signals; and aligning said first sequence samples in the template memory to that the R wave sample is stored in a predetermined sample location.

14. A method of detecting cardiac arrhythmias in a patient's heart, comprising the steps of:

sensing cardiac electrical signals when the heart is functioning in a known cardiac state;

characterizing said known cardiac state in a time sequence of template samples;

temporally compressing said time sequence of template samples;

storing said temporally compressed template samples;

monitoring a time sequence of cardiac electrical signal samples when the heart is functioning in an unknown cardiac state;

temporally compressing said unknown cardiac state samples monitored during said time sequence;

scan correlating said compressed unknown cardiac state samples with said stored compressed template samples to derive a correlation coefficient;

comparing said correlation coefficient with a threshold value; and classifying said unknown cardiac state within said known cardiac state when the correlation coefficient is greater than said threshold value, and classifying said unknown cardiac state outside said known cardiac state when the correlation coefficient is not greater than said threshold value, wherein each of said temporally compressing steps comprises the sub-steps of:

determining the differences between the most recent sample of said temporally compressed time sequence and each of a predetermined number of consecutive noncompressed samples of said sensed cardiac electrical signal sequence, wherein said predetermined number is a compression ratio;

mutually comparing said differences to identify the sample in said sensed cardiac electrical signal sequence associated with the largest difference; and setting the current compressed sample to the value of the identified sample.

15. Apparatus for detecting cardiac arrhythmias in a patient's heart, comprising:

means for sensing cardiac electrical signals when the heart is functioning in a known cardiac state;

means for characterizing said known cardiac state in a time sequence of template samples;

means for temporally compressing said time sequence of template samples;

means for storing said temporally compressed template samples;

means for monitoring a time sequence of cardiac electrical signal samples when the heart is functioning in an unknown cardiac state;

means for temporally compressing said unknown cardiac state samples monitored during said time sequence;

means for scan correlating said compressed unknown cardiac state samples with said stored compressed template samples to derive a correlation coefficient;

means for comparing said correlation coefficient with a threshold value;

means for classifying said unknown cardiac state within said known cardiac state when the correlation coefficient is greater than said threshold value, and classifying said unknown cardiac state outside said known cardiac state when the correlation coefficient is not greater than said threshold value; and means for highpass filtering said sensed cardiac electrical signals when the heart is operating in each of said known cardiac state and said unknown cardiac state to substantially eliminate the mean amplitude of each of said temporally compressed template samples and said temporally compressed unknown cardiac state samples.

16. Apparatus according to claim 15, wherein said means for scan correlating disregards the mean amplitude of each of said temporally compressed template samples and said temporally compressed unknown cardiac state samples when deriving said correlation coefficient.

17. Apparatus according to claim 16, wherein each of said temporally compressing means further comprises:
   means for subtracting each of a predetermined number of consecutive noncompressed samples of said sensed cardiac electrical signal from the most recently determined compressed sample, wherein said predetermined number is a compression ratio;
   means for storing each of said noncompressed samples and its associated absolute difference value from each subtraction result;
   means for mutually comparing each of said stored absolute difference values to determine the largest absolute difference; and
   means for setting the current compressed sample to the value of the stored noncompressed sample associated with the largest absolute difference.

18. Apparatus according to claim 17, wherein said means for characterizing said known cardiac state in a time sequence of template samples further comprises:
   means for sampling a first sequence of cardiac electrical signals sensed when the heart is functioning in a known cardiac state;
   means for storing said first sequence samples in a template memory;
   means for sampling and storing subsequent cardiac electrical signals;
   means for scan correlating said subsequent cardiac electrical signal samples with said template samples to derive a second correlation coefficient;
   means for comparing said second correlation coefficient with a second threshold value;
   means, operative when said second correlation coefficient is greater than said second threshold value, for aligning said subsequent cardiac electrical signal samples in time;
   means for averaging said aligned subsequent cardiac electrical signal samples into said template; and
   means for repeating said sampling, storing, scan correlating, comparing, aligning, and averaging means for a predetermined number of iterations.

19. Apparatus according to claim 18, further comprising:
   means for locating an R wave in said sequence of cardiac electrical signals; and
   means for aligning said first sequence samples in the template memory so that the R wave sample is stored in a predetermined sample location.

20. Apparatus according to claim 18, further comprising:
   means for monitoring said cardiac electrical signals to determine an intrinsic heart rate and its associated intrinsic cycle length; and
   means for setting a template length limit restricting the size of the template to a predetermined percentage of said intrinsic cycle length.

21. Apparatus according to claim 20, further comprising:
   means for locating an RF wave in said sequence of cardiac electrical signals; and
   means for aligning said first sequence samples in the template memory so that the R wave sample is stored in a predetermined sample location.

22. Apparatus according to claim 20, further comprising:
   means for sensing cardiac electrical signals when the heart is functioning in at least one additional known cardiac state;
   means for characterizing said at least one additional known cardiac state in a time sequence of template samples for each additional known cardiac state;
   means for temporally compressing said time sequence of template samples for each additional known cardiac state;
   means for storing said temporally compressed template samples for each additional known cardiac state;
   means for scan correlating those of said compressed unknown cardiac state samples which have been classified outside said known cardiac state with said stored compressed template samples for each additional known cardiac state to derive a correlation coefficient associated with each additional known cardiac state;
   means for mutually comparing each of said correlation coefficients with a threshold value; and
   means for classifying said unknown cardiac state within one of said additional known cardiac states according to said mutual comparison results.

23. Apparatus according to claim 22, wherein said first mentioned known cardiac state comprises normal sinus rhythm and at least one of said additional known cardiac states comprises ventricular tachycardia.

24. Apparatus for detecting cardiac arrhythmias in a patient's heart, comprising:
   means for sensing cardiac electrical signals when the heart is functioning in a known cardiac state;
   means for characterizing said known cardiac state in a time sequence of template samples;
   means for temporally compressing said time sequence of template samples;
   means for storing said temporally compressed template samples;
   means for monitoring a time sequence of cardiac electrical signal samples when the heart is functioning in an unknown cardiac state;
   means for temporally compressing said unknown cardiac state samples monitored during said time sequence;
   means for scan correlating said compressed unknown cardiac state samples with said stored compressed template samples to derive a correlation coefficient;

means for comparing said correlation coefficient with a threshold value; and means for classifying said unknown cardiac state within said known cardiac state when the correlation coefficient is greater than said threshold value, and classifying said unknown cardiac state outside said known cardiac state when the correlation coefficient is not greater than said threshold value, wherein each of said temporally compressing means further comprises:

means for determining the differences between the most recent sample of said temporally compressed time sequence and each of a predetermined number of consecutive noncompressed samples of said sensed cardiac electrical signal sequence, wherein said predetermined number is a compression ration;

means for mutually comparing said differences to identify the sample in said sensed cardiac electrical signal sequence associated with the largest difference; and means for setting the current compressed sample to the value of the identified sample.

25. Apparatus for detecting cardiac arrhythmias in a patient's heart, comprising:

means for sensing cardiac electrical signals when the heart is functioning in a known cardiac state;

means for characterizing said known cardiac state in a time sequence of template samples;

means for temporally compressing said time sequence of template samples;

means for storing said temporally compressed template samples;

means for monitoring a time sequence of cardiac electrical signal samples when the heart is functioning in an unknown cardiac state;

means for temporally compressing said unknown cardiac state samples monitored during said time sequence;

means for scan correlating said compressed unknown cardiac state samples with said stored compressed template samples to derive a correlation coefficient;

means for comparing said correlation coefficient with a threshold value; and means for classifying said unknown cardiac state within said known cardiac state when the correlation coefficient is greater than said threshold value, and classifying said unknown cardiac state outside said known cardiac state when the correlation coefficient is not greater than said threshold value, wherein said means for characterizing said known cardiac state in a time sequence of template samples further comprises:

means for sampling a first sequence of cardiac electrical signals sensed when the heart is functioning in a known cardiac state;

means for storing said first sequence samples in a template memory;

means for sampling and storing subsequent cardiac electrical signals;

means for scan correlating said subsequent cardiac electrical signals samples with said template samples to derive a second correlation coefficient;

means for comparing said second correlation coefficient with a second threshold value;

means, operative when said second correlation coefficient is greater than said second threshold value, for aligning said subsequent cardiac electrical signal samples in time;

means for averaging said aligned subsequent cardiac electrical signal samples into said template; and means for sequentially actuating said sampling, storing, scan correlating, comparing, aligning, and averaging means for a predetermined number of iterations.

26. Apparatus according to claim 25, further comprising:

means for monitoring said cardiac electrical signals to determine an intrinsic heart rate and its associated intrinsic cycle length; and means for setting a template length limit restricting the size of the template to a predetermined percentage of said intrinsic cycle length.

27. Apparatus according to claim 26, further comprising:

means for locating an R wave in said sequence of cardiac electrical signals; and means for aligning said first sequence samples in the template memory to that the R wave sample is stored in a predetermined sample location.

28. Apparatus according to claim 25, further comprising:

means for locating an R wave in said sequence of cardiac electrical signals; and means for aligning said first sequence samples in the template memory to that the R wave signals is stored in a predetermined sample location.

* * * * *